United States Patent [19]

Phillips

[11] 4,167,334

[45] Sep. 11, 1979

[54] FLAME HEAD FOR FLAME PHOTOMETRIC DETECTOR USED IN GAS CHROMATOGRAPHY

[75] Inventor: Lawrence D. Phillips, Caney, Kans.

[73] Assignee: Phillips Petroleum Co., Bartlesville, Okla.

[21] Appl. No.: 891,979

[22] Filed: Mar. 30, 1978

[51] Int. Cl.² .................. G01N 21/58; G01N 31/08
[52] U.S. Cl. .................................. 356/315; 356/417; 422/89; 422/91
[58] Field of Search ............ 23/232 R, 232 E, 254 R, 23/254 E, 255 R, 255 E; 356/87, 187; 250/554, 227; 431/4, 126; 422/54, 89, 91

[56] References Cited

U.S. PATENT DOCUMENTS

| | | | |
|---|---|---|---|
| 3,086,848 | 4/1963 | Reinecke | 23/254 EF |
| 3,141,741 | 7/1964 | Hoel et al. | 23/253 PC |
| 3,298,785 | 1/1967 | Reul | 23/253 PC X |
| 3,330,960 | 7/1967 | Rich | 250/554 |
| 3,372,000 | 3/1968 | Gallaway et al. | 23/254 EF |
| 3,455,657 | 7/1969 | Jentzsch et al. | 23/232 E X |
| 3,473,895 | 10/1969 | Brittan et al. | 23/255 E X |
| 3,489,498 | 1/1970 | Brody et al. | 356/187 |
| 3,489,523 | 1/1970 | Clardy et al. | 23/232 E |
| 3,504,976 | 4/1970 | Gilbert, Jr. | 23/254 R X |
| 3,597,162 | 8/1971 | Reinecke | 23/232 E X |
| 3,644,743 | 2/1972 | Binek et al. | 356/187 X |
| 3,661,533 | 5/1972 | David et al. | 23/232 E X |
| 3,692,415 | 9/1972 | Schiller | 356/187 |

Primary Examiner—Joseph Scovronek

[57] ABSTRACT

A flame head for a flame photometric detector is disclosed comprising an explosion-proof housing having a combustion chamber therein defined by a fused quartz tube flame wall barrier. Means are provided for securing a fiber-optic bundle to the housing with one terminal end of the fiber-optic bundle positioned adjacent the fused quartz tube whereby light emitted from the combustion chamber can be transmitted via the fiber-optic bundle to a photomultiplier and associated electronic detection means remotely located therefrom. A burner tip communicates with one end of the fused quartz tube and provides gas effluent and fuel through a passage therein coaxially aligned with the quartz tube while providing required air to four circumferentially spaced ports disposed about the passage. Means are also provided for purging fuel from the area immediately adjacent the terminal end of the fiber-optic bundle adjacent the quartz tube.

15 Claims, 5 Drawing Figures

FLAME HEAD FOR FLAME PHOTOMETRIC DETECTOR USED IN GAS CHROMATOGRAPHY

The present invention relates to the analysis of gases. In one aspect the invention relates to an improved detector for analyzing gases. In another aspect the invention relates to an improved photodetection flame head for use in gas analysis.

Gas chromatographic detectors are utilized for quantitative or qualitative analysis of constituents of a gaseous sample. Detectors are known which measure various physical and chemical properties of elements and compounds, such as thermal conductivity, differences in the speed of sound transmission in a selected medium, electron capture ability, amount of ion current produced under combustion and observation, and light emission wavelengths and intensity produced by flame excitation.

Combustion or flame detectors are of two basic types, namely flame ionization detectors and flame emission detectors. Flame emission detectors utilize a flame to excite the atoms of sample constituents to higher energy states. As the energy states return to previous normal levels, characteristic wavelengths of light are emitted from the sample and measured by photometric or other light analysis methods. Those flame emission detectors which measure wavelengths of light emitted from the sample by photometric methods are commonly referred to as flame photometric detectors.

It is desirable to utilize a flame photometric detector with a gas chromatographic analysis system for the continuous sampling of gases in an ongoing process. In order to utilize a flame photometric detector in process gas chromatography, it is necessary that such a flame photometric detector be designed to meet the explosion-proof requirements of Underwriter' Laboratory Code publication UL886.

It is also extremely important in the design of flame photometric detectors to eliminate or reduce to the maximum amount possible the presence of hydrogen at the terminal end of a fiber-optic light transmission medium coupled to the flame head in order to maximize the life of the fiber-optic light transmission medium. The presence of hydrogen on the fiber-optic medium causes severe degradation of the fiber-optic medium in a very short period of time.

It is therefore an object of the present invention to provide an improved flame photometric detector which can be employed in process gas chromatography.

Another object of the invention is to provide an improved flame head for a flame photometric detector which meets explosion-proof requirements for process flame emission photometry.

Yet another object of the invention is to provide a flame head which eliminates the presence of hydrogen at the terminal end of a fiber-optic bundle adjacent the combustion chamber.

Another object of the invention is to provide a flame head which overcomes the deficiencies of similar prior art devices.

Yet another object of the invention is to provide a flame photometric detector which overcomes the deficiencies of similar prior art devices.

Still another object of the invention is to provide a flame head which is economical in construction and operation.

Other aspects, objects and advantages of the present invention will be evident upon reference to the specification, claims and drawings in which:

In accordance with one aspect of the present invention an improved photodetection flame head is provided having a body with a combustion chamber therein at least partially defined by a translucent barrier tube. A burner tip having a plurality of passages therethrough communicates with one end of the combustion chamber. A first conduit communicates between the burner tip and a source of gas to be analyzed, while a second conduit communicates between the burner tip and the source of pressurized hydrogen. A passage communicates between the burner tip and the source of pressurized oxygen. One end of a light transmission waveguide is positioned adjacent the exterior of the barrier tube to transmit light from the combustion chamber through the light transmission waveguide. An exhaust passage is also provided between the interior of the combustion chamber and the exterior of the body.

In accordance with another aspect of the invention, an improved flame photometric detector is provided wherein a source of hydrogen is connected to the burner tip of the photodetection flame head described above by a suitable conduit and a chromatographic column is connected to the burner tip whereby effluent gas from the column is conducted to the tip. The fiber-optic light transmission bundle is connected between the flame head body and a photomultiplier tube which receives light from the fiber-optic bundle and provides a signal output in response thereto to a detector which detects the presence of at least one element in the effluent gas in response to the signal output from the photomultiplier tube.

Figure 1:
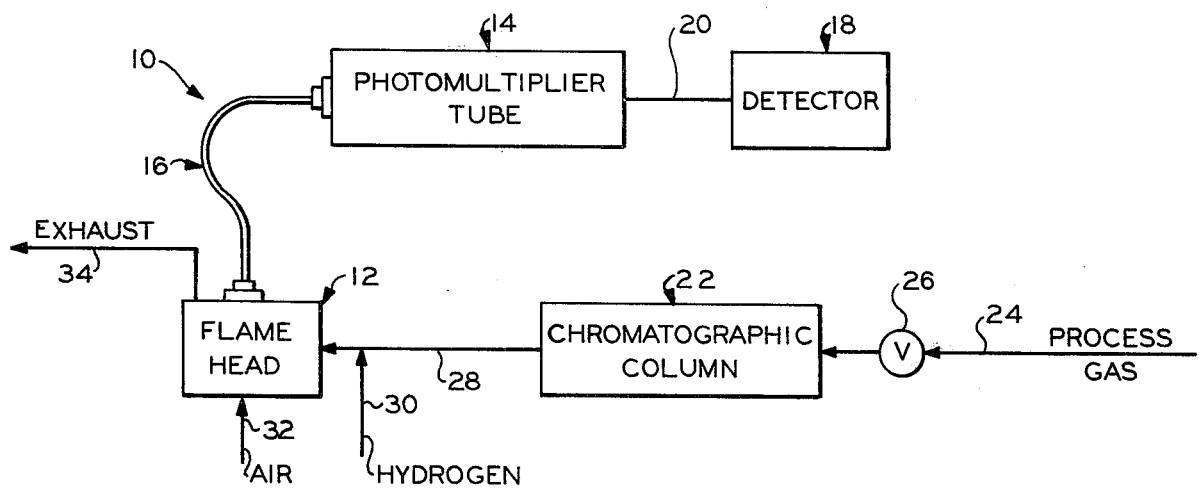
FIG. 1 is a schematic illustration of a flame photometric detector system constructed in accordance with the present invention.
Figure 2:
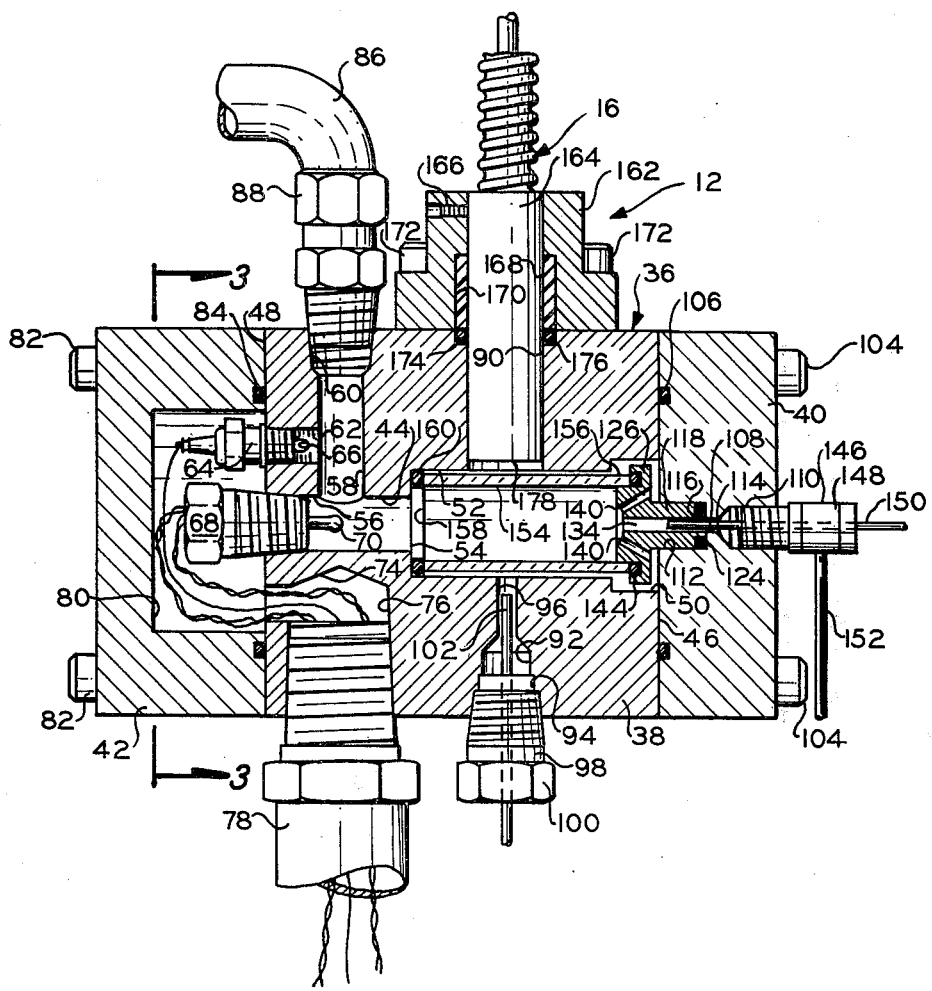
FIG. 2 is a cross-sectional view of a preferred embodiment of a photodetection flame head constructed in accordance with the present invention.
Figure 3:
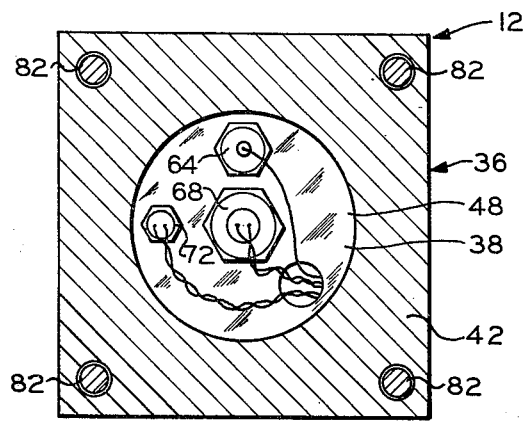
FIG. 3 is a cross-sectional view taken along line 3—3 of FIG. 2.
Figure 4:
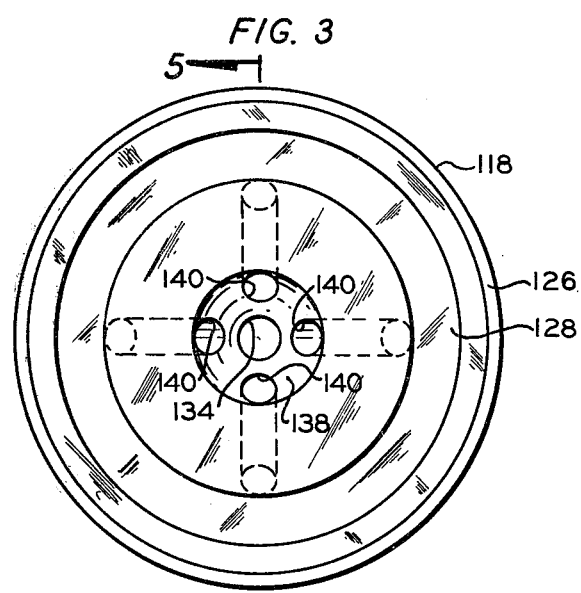
FIG. 4 is an enlarged end elevation view of the burner tip as viewed from the combustion chamber of the photodetection flame head in FIG. 2.
Figure 5:
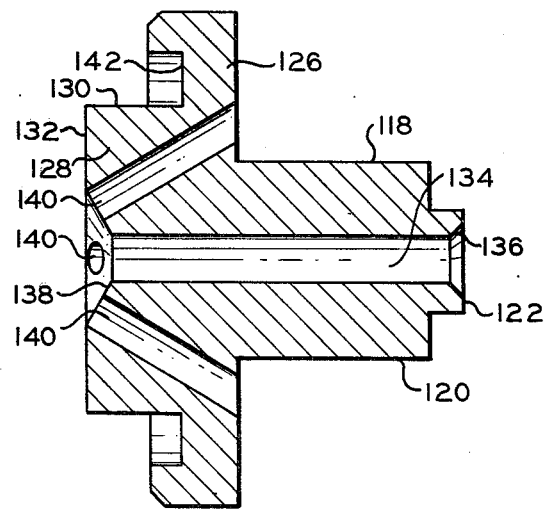
FIG. 5 is a cross-sectional view taken along line 5—5 of FIG. 4.

Referring now to the drawings, FIG. 1 schematically illustrates a flame photometric detector system 10 which includes a photometric flame head 12 connected to a photomultiplier tube 14 via a light transmission waveguide 16, preferably a fiber-optic light transmission bundle 16. The output of the photomultiplier tube is connected to a suitable detector 18 via electrical conductor 20. A chromatographic column 22 constantly monitors process gas which is provided to the chromatographic column via conduit 24 and a suitable control valve 26 interposed in the conduit 24. Column effluent gas is conducted from the chromatographic column to the flame head 12 via conduit 28. A suitable fuel, preferably hydrogen, is provided from a suitable source to the flame head 12 via conduit 30, while air is provided to the flame head from a suitable source via conduit 32 to provide oxygen to support combustion. Exhaust gas from the combustion chamber in the flame head 12 exits therefrom via exhaust conduit 34.

The photomultiplier tube 14 can be of conventional construction and is provided with band pass means to render it sensitive to a predetermined light wavelength corresponding to a particular element, the presence of which in the column effluent it is important to know. Typically, the photomultiplier tube can be adjusted to respond to the presence of sulfur and/or phosphorous constituents in the column effluent gas.

The detector 18 can also be of conventional construction and is typically capable of recording and analyzing the output from the photomultiplier tube.

Referring now to FIGS. 2, 3, 4 and 5, a preferred embodiment of the photometric flame head 12 is illustrated therein. The photometric flame head comprises a body assembly 36 which includes a main body member 38, a base plate 40 and a cap plate 42.

The main body member 38 is provided with a longitudinal passage 44 extending therethrough and communicating with opposite end faces 46 and 48 of the main body member. The longitudinal passage includes a first counterbore 50 which intersects the end face 46 and a second counterbore 52 which communicates with the first counterbore and extends therefrom toward the end face 48 terminating in an annular wall 54 facing the first counterbore. Internal threads 56 are formed in the end portion of the passage 44 communicating with the end face 48.

A lateral exhaust passage 58 communicates between the exterior of the main body member 38 and the longitudinal passage 44 intermediate the annular wall 54 in the internal threads 56. Internal threads 60 are formed in the exhaust passage 58 and communicate with the exterior of the main body member. An internally threaded igniter passage 62 communicates between the exhaust passage 58 and the end face 48 of the main body member 38.

An igniter 64, preferably in the form of a conventional glow plug, such as the type used in small displacement model airplane engines, is threadedly secured within the igniter passage 62 with the heater element 66 thereof extending toward the exhaust passage 58. A thermistor 68 is threadedly secured within the internal threads 56 of the longitudinal passage 44 with the probe 70 thereof extending into the longitudinal passage therefrom. A suitable thermistor for this application is manufactured by Victory Engineering Corp., Springfield, N.J. and is identified by the model No. SF14-51A11. A cartridge heater 72 is mounted in a blind cavity (not shown) formed in the main body member 38 in parallel alignment with the longitudinal passage 44.

An L-shaped passage 74 communicates between the end face 48 of the main body member adjacent the thermistor 68 and the exterior of the main body member. Internal threads 76 are formed in the passage 74 and communicate with the exterior of the main body member. A metallic electrical conduit 78 is threadedly secured to the internal threads 76. Electrical leads from appropriate remotely located sources (not shown) are routed through the conduit 78 and passage 74 to the glow plug 64, thermistor 68 and cartridge heater 72. The glow plug, thermistor, cartridge heater and leads associated therewith are fully enclosed within a cavity 80 formed in the cap plate 42, which cap plate is secured to the end face 48 of the main body member by means of four threaded bolts 82. A suitable seal is provided between the cap plate and the main body member by means of a resilient annular seal 84, such as a Viton O-ring, carried in a corresponding annular groove formed in the cap plate. An exhaust conduit 86 is threadedly secured to the internal threads 60 of the exhaust passage 58. Exhaust conduit 86 is provided with an inline flame arrester 88 and provides means for connection between the flame head 12 and the exhaust conduit 34 of the flame photometric detector system 10. A suitable flame arrester for this application is manufactured by Hoke, Inc., Kresskill, N.J.

A lateral passage 90 communicates between the second counterbore 52 and the exterior of the main body member 38. A second lateral passage 92 also communicates between the second counterbore 52 and the exterior of the main body member 38. The lateral passage 90 is adapted to receive the terminal end of a fiber-optic light transmission bundle. The second lateral passage 92 provides an inlet into the main body member 38 for combustion air.

The second lateral passage 92 is provided with an internally threaded portion 94 communicating with the exterior of the main body member 38. The interior portion 96 of the passage 92 communicating with the counterbore 52 is of substantially reduced diameter. An air inlet assembly 98 is threadedly secured in the internally threaded portion 94. The air inlet assembly 98 includes an externally threaded fitting 100 with a longitudinal passage extending therethrough. A length of stainless steel capillary tubing 102 having an inside diameter of approximately 0.015 inch (0.038 cm.) extends through the longitudinal passage of the fitting 100 and is brazed thereto to provide a seal therewith. The inner end of the capillary tube 102 extends to a point near but not beyond the wall of the second counterbore 52. The capillary tube 102 provides means for connecting the air inlet assembly 98 to the conduit 32 from a source of air for the flame head to provide oxygen for combustion.

The base plate 40 is secured to the end face 46 of the main body member 38 by means of four threaded bolts 104. A suitable seal is achieved between the base plate 40 and the end face 46 by means of a resilient annular seal member 106, such as a Viton O-ring, carried in a corresponding annular groove formed in the base plate.

A longitudinal passage 108 extends through the base plate 40 and is coaxially aligned with the longitudinal passage 44 of the main body member 38. The longitudinal passage 108 includes an internally threaded portion 110 which communicates with the exterior of the base plate 40. A counterbore 112 is formed in the opposite end of the longitudinal passage 108 and communicates with the longitudinal passage 44 of the main body member. Longitudinal passage 108 further includes a medial portion 114 of substantially reduced diameter extending between the counterbore 112 and the internally threaded portion 110. The counterbore 112 forms an annular wall 116 which communicates with the medial portion 114.

A burner tip 118 is mounted in the base plate 40. The burner tip 118 is provided with a cylindrically shaped end portion 120 which is closely received within the counterbore 112 of the base plate. The end face 122 of the burner tip abuts the annular wall 116 of counterbore 112. A suitable seal is provided by a resilient annular seal member 124, preferably a Viton O-ring, mounted in a corresponding annular recess formed in the end face 122 of the burner tip. A radially extending flange 126 is formed on the opposite end portion 128 of the burner tip. A cylindrical surface 130 is formed on the flange 126 and communicates with the opposite end face 132 of the burner tip.

A longitudinal passage 134 extends through the burner tip 118 and communicates with the end face 122 via a chamfered surface 136 while communicating with the opposite end face 132 via a frustoconical surface 138 having an apical angle of about 120°. The axis of the longitudinal passage 134 is coaxially aligned with the longitudinal passage 44 of the main body member 38 and the longitudinal passage 108 of the base plate 40. Four cylindrically shaped peripheral passages 140 circumferentially spaced about the central longitudinal passage 134 extend through the flange 126 and communicate with the frustoconical surface 138. The axes of the passages 140 mutually intersect the axis of the longitudinal passage 134 at approximately the same point within the longitudinal passage 44 of the main body member 38. The axis of each passage 140 intersects the axis of the longitudinal passage 134 at an angle of approximately 30 degrees. An annular recess 142 is formed in the flange 126 and carries a resilient annular seal member 144, preferably a Viton O-ring, therein.

A carrier and hydrogen inlet assembly 146 comprising an externally threaded fitting 148 is threadedly secured within the internally threaded portion 110 of the longitudinal passage through the base plate 40. The assembly 146 includes a first capillary tube 150, having an inside diameter of approximately 0.015 inch (0.038 cm.), which extends entirely through a longitudinal passage in the fitting 148 and which is brazed to the fitting to achieve a seal therewith. The innermost end portion of the first capillary tube 150 extends through the longitudinal passage 108 of the base plate and a substantial distance into the longitudinal passage 134 of the burner tip 118. A second capillary tube 152, having an inside diameter of approximately 0.015 inch (0.038 cm.), is received in a lateral passage formed in and communicating with the longitudinal passage through the fitting 148 and communicates with the interior of the first capillary tube 150 within the fitting 148. The second capillary tube 152 is brazed to the fitting 148 to achieve a suitable seal therewith.

The first capillary tube 150 provides means for connection between the flame head 12 and the conduit 28 conducting carrier or column effluent gas from the chromatographic column 22 to the flame head. Similarly, the second capillary tube 152 provides means for connecting the flame head 12 to the conduit 30 from a source of hydrogen. The fitting 146 thus provides means for conducting carrier or effluent gas and hydrogen to the longitudinal passage 44 in the main body member 38 via the longitudinal passage 134 in the burner tip 118.

A translucent cylindrical tube 154, preferably formed of transparent fused quartz, is concentrically positioned within the second counterbore 52 of the longitudinal passage 44 in the main body member 38. One end portion 156 of the tube 154 is closely received over the cylindrical outer surface 130 of the burner tip 118 and the end face thereof is in sealing engagement with the resilient annular seal 144. The opposite end face 158 of the tube 154 sealingly engages a resilient annular seal member 160, preferably a Viton O-ring, positioned between the end face 158 and the annular wall 54 in the longitudinal passage 44 of the main body member 38.

The transparent cylindrical tube 154 provides a flame barrier tube structure which defines a combustion chamber in conjunction with the longitudinal passage 44 and the burner tip 118.

The fiber-optic light transmission bundle 16 is provided with a mounting flange secured to one end portion 164 thereof by means of a threaded set screw 166 mutually engaging the light transmission bundle 16 and the mounting flange 162. The light transmission bundle is additionally secured to the mounting flange 162 by means of suitable potting compound 168 deposited and cured in an annular cavity 170 formed in the flange 162 and surrounding the end portion 164 of the light transmission bundle 16. The flange 162 is secured to the main body member 138 by means of four threaded bolts 172. A fluid tight seal is achieved among the main body member 38, mounting flange 162 and light transmission bundle 16 by means of a resilient annular seal member 174, preferably a Viton O-ring, disposed in an annular recess 176 formed in the main body member 38 in communication with the lateral passage 90.

The terminal end 178 of the fiber-optic light transmission bundle 16 is positioned proximate to the exterior surface of the transparent cylindrical barrier tube 154.

In the operation of the flame photometric detector system 10, carrier or effluent gas from the chromatographic column 22 is directed into the interior of the transparent barrier tube 154 via the conduit 28, capillary tube 150 and longitudinal passage 134 of the burner tip 118. A suitable fuel, preferably hydrogen, from a suitable source is provided to the interior of the barrier tube 154 via conduit 30, capillary tube 152, capillary tube 150 and the longitudinal passage 134 of the burner tip 118. Oxygen to support combustion within the barrier tube 154 is provided from a suitable air source via conduit 32, capillary tube 102, the interior portion 96 of second lateral passage 92, the annular space between the exterior of the barrier tube 154 and the counterbores 50 and 52 of the longitudinal passage 44 and the passages 140 of the burner tip 118.

The routing of the combustion supporting air through the annular space between the barrier tube and the second counterbore 52 serves to purge the area at the juncture of the terminal end 178 of the fiber-optic light transmission bundle 16 and the exterior surface of the transparent barrier tube 154 of hydrogen in order to maximize the life of the fiber-optic light transmission medium since the presence of hydrogen on the fiber-optic medium would otherwise cause severe degradation of the fiber-optic medium is a very short period of time. Thus the continuous introduction of air during the operation of the photometric flame head 12 provides a resulting continuous purging of any other gases such as hydrogen which might otherwise accumulate at the terminal end 178 of the fiber-optic light transmission bundle 16.

Owing to the configuration of the burner tip 118, the gas streams of effluent gas, hydrogen and air are mixed together within the transparent barrier tube 154 of the combustion chamber. A combustible mixture of these gases is ignited by the glow plug heater element 66 which is heated electrically to the combustion temperature of the gas mixture. The thermistor 68 provides a signal to a suitable external monitoring device to indicate whether or not combustion is taking place within the combustion chamber of the flame head 12. In the event a signal is received indicating combustion is no longer taking place, current is applied to the glow plug to ignite the gas mixture. When the thermistor indicates that combustion is taking place, current is no longer applied to the glow plug.

Under certain circumstances, the photometric flame head 12 is maintained within a heated environment, such as an oven, wherein the flame head is maintained at all times at a temperature above the condensation temperature of water vapor. However, it may be desirable or necessary to operate the photometric flame head 12 in an environment wherein the ambient air surrounding the flame head is at a temperature below the condensation temperature of water vapor. Under such conditions, electric current is provided to the cartridge heater 72 to maintain the flame head 12 at a temperature above the condensation temperature of water vapor so that water produced in the combustion process within the combustion chamber remains in the vapor state until exhausted from the flame head 12, thus preventing degradation of flame head performance as a result of the condensation of water produced as a constituent of the combustion products in the flame head.

The main body member 38, base plate 40, cap plate 42, burner tip 118 and mounting flange 162 are all preferably made from aluminum. It will be understood, however, that other metals, such as stainless steel, can be advantageously employed for the construction of these parts.

In a preferred embodiment, the diameter of the longitudinal passage 134 of the burner tip 118 is about 0.078 inch (0.198 cm.) and the diameters of the passages 140 of the burner tip 118 are about 0.062 inch (0.157 cm.). This configuration of the burner tip 118 has been found to provide optimized performance of the flame photometric detector system 10 while minimizing the flow rates of hydrogen and air for optimum signal peak. In this configuration, the optimum flow rate of hydrogen has been found to be about 51.7 cubic centimeters per minute while the optimum flow rate of air was found to be about 48.3 cubic centimeters per minute. Under these optimized conditions, the flame photometric detector system 10 provided a 68.7 percent decrease in hydrogen flow rate and a 58 percent decrease in air flow rate when compared to a typical laboratory chromatograph photometric flame detector.

Under these optimized conditions the effluent from the chromatographic column 22 of a gas chromatograph is mixed with hydrogen and burned with air within the combustion chamber of the flame head 12. The otimized hydrogen/air flow ratio described above provides a reducing atmosphere. The flame in the combustion chamber allows $S_2$ or HPO species to be produced when sulfur or phosphorous containing compounds elute from the chromatographic column. The $S_2$ and HPO species chemiluminesce in the region above the flame within the transparent flame barrier tube 154. This emitted light is gathered and transmitted by the fiber-optic light transmission bundle 16 via the transparent flame barrier 154 through a narrow band pass filter (394 nm for sulfur and 526 nm for phosphorous) into the photocathode of the photomultiplier tube 14. The output current of the photomultiplier tube is proportional to the square of the sulfur concentration and is directly proportional to the phosphorous concentration. This current is amplified and converted to a voltage within the detector 18.

The flame head 12, constructed as described above, complies with Underwriters' Laboratory Code UL 886 for hazardous locations. Thus, the flame head 12 can be advantageously employed to provide continuous flame photometric detection of effluent gas from a chromatographic column which is employed in the continuous analysis of process gas.

Changes may be made in the combination and arrangement of parts or elements as heretofore set forth in the specification and shown in the drawings without departing from the spirit and scope of the invention as defined in the following claims.

What is claimed is:

1. A photodetection flame head comprising:
    a body having a combusiton chamber therein;
    a translucent barrier tube carried by said body, the interior of said barrier tube defining at least a portion of said combustion chamber;
    a burner tip communicating with said combustion chamber and having a central passage therethrough communicating with the interior of said combustion chamber, and a plurality of peripheral passages therethrough and circumferentially spaced about said central passage, said peripheral passages communicating with the interior of said combustion chamber;
    conduit means communicating the central passage of said burner tip, a source of fuel, and a source of fluid to be analyzed;
    passage means communicating between the peripheral passages of said burner tip and a source of oxygen;
    fiber-optic light transmission means having first and second end portions with the first end portion thereof positioned adjacent the exterior of said barrier tube for transmitting light from said combustion chamber through said fiber-optic light transmission means; and
    an exhaust passage communicating between the interior of said combustion chamber and the exterior of said body.

2. A photodetection flame head as defined in claim 1 wherein said translucent barrier tube is formed of fused quartz.

3. A photodetection flame head as defined in claim 1 wherein said passage means additionally communicates with the first end portion of said fiber-optic light transmission means adjacent the exterior of said translucent barrier tube.

4. A photodetection flame head as defined in claim 1 wherein the axes of said peripheral passages each mutually intersect the axis of said central passage at an angle of about 30 degrees at a common point within said combustion chamber.

5. A photodetection flame head as defined in claim 1 wherein said exhaust passage is characterized further to include means therein for preventing the propagation of a flame therepast from said combustion chamber.

6. A photodetection flame head as defined in claim 1 characterized further to include ignition means carried within said body for igniting combustible mixtures in said combustion chamber.

7. A photodetection flame head as defined in claim 1 characterized further to include heating means carried by said body for maintaining the temperature of said flame head above the condensation point of water vapor.

8. A flame head comprising:
    a body having a longitudinal passage extending therethrough;
    a fused quartz flame barrier tube having opposite ends disposed in said passage and defining at least a portion of a combustion chamber therein;
    a burner tip communicating with one end of said barrier tube, said burner tip having a central passage therethrough coaxially aligned with the longitudinal axis of the longitudinal passage of said body and having a plurality of passages circumferentially spaced around said central passage, the axes of said central passage and said circumferentially spaced passages converging at a point within said barrier tube;

means communicating between said central passage of said burner tip and a source of fuel and a source of fluid to be analyzed;

fiber-optic light transmission means having a terminal end thereof positioned adjacent the exterior of said barrier tube and extending therefrom through said body to a remote location for transmitting light from said combustion chamber to the remote location;

a purge passage communicating between the exterior of said barrier tube adjacent the terminal end of said fiber-optic light transmission means and the ends of said circumferentially spaced passages remote from said barrier tube;

means communicating between said purge passage and a source of oxygen;

means adjacent the end of said flame barrier opposite said burner tip for igniting gases in said combustion chamber; and an exhaust passage communicating between the interior of said combustion chamber and the exterior of said body.

9. A flame photometric detector for monitoring process stream effluent fluid from a chromatographic column during the operation of the process, comprising:
a body;
a combustion chamber having opposite ends and housed in said body;
a translucent barrier tube in said body defining at least a portion of said combustion chamber;
a burner tip communicating with one end of said combustion chamber, said burner tip having a central passage therethrough substantially aligned with said combustion chamber and having a plurality of peripheral passages therethrough circumferentially spaced about said central passage;
first conduit means communicating between said central passage of said burner tip and said chromatographic column for conducting effluent fluid from said chromatographic column to said combustion chamber via said central passage of said burner tip;
second conduit means communicating between said central passage of said burner tip and a source of fuel for conducting fuel to said combustion chamber via said central passage of said burner tip;
light fiber-optic transmission means having first and second end portions with the first end portion thereof positioned adjacent the exterior of said barrier tube for transmitting light emitted from the interior of said barrier tube to the second end portion of said fiber-optic light transmission means;
photomultiplier means in light receiving communication with the second end portion of said light transmission means for receiving light therefrom and providing a signal output in response thereto;
detection means connected to said photomultiplier means for receiving the signal output from said photomultiplier means and detecting the presence of at least one component in said effluent fluid in response to said signal output;
oxygen passage means in said body communicating between said peripheral passages of said burner tip and a source of air for conducting oxygen to said combustion chamber via said peripheral passages; and
exhaust passage means communicating between said combustion chamber and the exterior of said body for conducting products of combustion therethrough.

10. A flame photometric detector as defined in claim 9 wherein said oxygen passage means further communicates with the first end portion of said fiber-optic light transmission means adjacent the exterior of said barrier tube whereby fuel adjacent the first end portion of said fiber-optic light transmission means is purged therefrom as oxygen is conducted through said oxygen passage means to said combustion chamber.

11. A flame photometric detector as defined in claim 9 characterized further to include:
heating means carried by said body for maintaining the temperature of said combustion chamber and said exhaust passage means at a temperature above the condensation point of water.

12. A flame photometric detector as defined in claim 9 characterized further to include:
ignition meas positioned proximate to said combustion chamber for igniting gases in said combustion chamber.

13. A flame photometric detector as define in claim 9 characterized further to include:
exhaust flame arrestor means communicating with said exhaust passage means for preventing flame propagation therepast from said combustion chamber.

14. A flame photometric detector as defined in claim 9 wherein said translucent barrier tube is formed of fused quartz.

15. A flame photometric detector system for analyzing process stream effluent fluid from a chromatographic column during operation of process, comprising:
a photodetection flame head comprising:
a body having a combustion chamber therein;
a translucent barrier tube in said body, the interior of said barrier tube surrounding at least a portion of said combustion chamber;
a burner tip communicating with said combustion chamber and having a central passage therethrough communicating with the interior of said combustion chamber, and a plurality of peripheral passages therethrough and circumferentially spaced about said central passage, said peripheral passages communicating with the interior of said combustion chamber;
fiber-optic light transmission means having first and second end portions with the first end portion thereof positioned adjacent said barrier tube for transmitting light emitting therefrom to the second end portion of said fiber-optic light transmission means;
inlet passage means communicating between the peripheral passages of said burner tip and the exterior of said barrier tube; and
exhaust passage means communicating between said combustion chamber and the exterior of said body;
means for conducting fuel to the central passage of said burner tip;
means for conducting said effluent fluid to the central passage of said burner tip;

photomultiplier means in light receiving communication with the second end portion of said fiber-optic light transmission means for receiving light therefrom and providing a signal output in response thereto;

detection means connected to said photomultiplier means for receiving the signal output from said photomultiplier means and detecting the presence of at least one component of said effluent fluid in response thereto; and means for conducting oxygen to said inlet passage means.

* * * * *

UNITED STATES PATENT AND TRADEMARK OFFICE
CERTIFICATE OF CORRECTION

PATENT NO. : 4,167,334

DATED : September 11, 1979

INVENTOR(S) : Lawrence D. Phillips

It is certified that error appears in the above-identified patent and that said Letters Patent are hereby corrected as shown below:

Column 9, claim 9, line 51, "light fiber-optic transmission" should be --- fiber-optic light transmission ---.
Column 9, claim 9, line 58, after "said" and before "light" insert --- fiber-optic ---.
Column 10, claim 12, line 23, after "ignition" and before "positioned", "meas" should be --- means ---.

Signed and Sealed this

Tenth Day of March 1981

[SEAL]

Attest:

RENE D. TEGTMEYER

Attesting Officer     Acting Commissioner of Patents and Trademarks